(12) United States Patent
Maxted et al.

(10) Patent No.: US 7,736,534 B2
(45) Date of Patent: Jun. 15, 2010

(54) PHOSPHORESCENT COMPOSITIONS AND ORGANIC LIGHT EMITTING DEVICES CONTAINING THEM

(75) Inventors: Neil Maxted, Oxford (GB); Annette Steudel, Cambridge (GB); Alan Mosley, Hertfordshire (GB); Mark D. Andrews, Oxford (GB); Kai Look, Oxford (GB); Nigel Male, Cambridge (GB)

(73) Assignee: CDT Oxford Limited, Cambridgeshire (GB)

( * ) Notice: Subject to any disclaimer, the term of this patent is extended or adjusted under 35 U.S.C. 154(b) by 1148 days.

(21) Appl. No.: 10/506,914

(22) PCT Filed: Mar. 3, 2003
(Under 37 CFR 1.47)

(86) PCT No.: PCT/GB03/00857
§ 371 (c)(1),
(2), (4) Date: May 23, 2005

(87) PCT Pub. No.: WO03/074628
PCT Pub. Date: Sep. 12, 2003

(65) Prior Publication Data
US 2006/0083943 A1    Apr. 20, 2006

(30) Foreign Application Priority Data
Mar. 4, 2002 (GB) ................................ 0204989.8

(51) Int. Cl.
C09K 11/06 (2006.01)
H01L 51/54 (2006.01)
H01L 51/56 (2006.01)

(52) U.S. Cl. ............... 252/301.35; 427/66; 313/506; 428/917; 526/171; 526/258; 526/259; 528/412; 528/422; 528/423

(58) Field of Classification Search ............... 428/690, 428/917; 427/58, 66; 313/502–509; 257/E51.001–E51.052, 40, 88–103; 252/301.16–301.35
See application file for complete search history.

(56) References Cited

U.S. PATENT DOCUMENTS

| | | | | |
|---|---|---|---|---|
| 4,834,505 | A | * | 5/1989 | Migliorato et al. ............ 349/48 |
| 5,518,824 | A | | 5/1996 | Funhoff et al. ............... 428/690 |
| 5,814,244 | A | | 9/1998 | Kreuder et al. ......... 252/301.16 |
| 5,922,481 | A | | 7/1999 | Etzbach et al. ............. 428/690 |
| 5,929,194 | A | | 7/1999 | Woo et al. ................... 528/229 |
| 6,150,043 | A | * | 11/2000 | Thompson et al. .......... 428/690 |
| 6,303,238 | B1 | | 10/2001 | Thompson et al. .......... 428/690 |
| 6,416,915 | B1 | * | 7/2002 | Kikuchi et al. ............... 430/56 |
| 6,696,181 | B2 | * | 2/2004 | Okunaka et al. ............ 428/690 |
| 7,396,598 | B2 | * | 7/2008 | Takeuchi et al. ............ 428/690 |
| 2001/0019782 | A1 | | 9/2001 | Igarashi et al. .............. 428/690 |
| 2002/0041979 | A1 | * | 4/2002 | Taguchi ...................... 428/690 |

FOREIGN PATENT DOCUMENTS

| | | |
|---|---|---|
| EP | 891 121 A1 | 1/1999 |
| JP | 2000-256319 | * 9/2000 |
| JP | 2001-257076 | 9/2001 |
| WO | WO 00/57676 | 9/2000 |
| WO | WO 01/49769 A1 | 7/2001 |

OTHER PUBLICATIONS

Lamansky et al., "Molecularly doped polymer light emitting diodes utilizing phosphorescent Pt(II) and Ir(III) dopants," Organic Electronics, vol. 2, No. 1, pp. 53-62, Mar. 2001.*

D'Andrade et al., "Controlling Exciton Diffusion in Multilayer White Phosphorescent Organic Light Emitting Devices," Advanced Materials, vol. 14, No. 2, pp. 147-151, Jan. 2002.*

Bayerl, et al., "Crosslinkable Hole-Transport Materials for Preparation of Multilayer Organic Light Emitting Devices by Spin-Coating," Macromol. Rapid Commun., vol. 20, pp. 224-228 (1999).

"Photo-Cross-Linked Triphenylenes as Novel Insoluble Hole Transport Materials in Organic LEDs", Bacher et al., Macromolecules 32, 1999, pp. 4551-4557.

(Continued)

Primary Examiner—Marie R. Yamnitzky
(74) Attorney, Agent, or Firm—Marshall, Gerstein & Borun LLP

(57) ABSTRACT

Compositions of a mixture of (A) a polymerizable compound, which undergoes polymerization on exposure to heat or to actinic radiation, having the general formula $$Q{-}[(L)_m{-}X]_n$$

wherein Q is an organic charge transporting fragment, L is a linker group, X is a group capable of undergoing free radical or anionic polymerization on exposure to heat or actinic radiation, m is 0 or 1, and n is an integer having a value of 2 or more; and (B) a phosphorescent material are described, as is an organic light-emitting diode (OLED) device comprising at least one emissive layer that has been formed by polymerizing such a composition. A method for forming an OLED, including depositing a layer containing the polymerizable composition from solution and exposing the layer to heat or actinic radiation to induce polymerization, is also disclosed.

19 Claims, 1 Drawing Sheet

OTHER PUBLICATIONS

"Very High-Efficiency Green Organic Light-Emitting Devices Based on Electrophosphorescence", Baldo et al., Applied Physics Letters, vol. 75, No. 1, Jul. 5, 1999, pp. 4-6.

"High-Efficiency Red Electrophosphorescence Devices", Adachi et al., Applied Physics Letters, vol. 78, No. 11, pp. 1622-1624.

International Search Report in PCT/GB03/00857 dated Jun. 16, 2003.

Search Report in GB 0204989.8 dated Nov. 22, 2002.

* cited by examiner

PHOSPHORESCENT COMPOSITIONS AND ORGANIC LIGHT EMITTING DEVICES CONTAINING THEM

This is the U.S. national phase of International Application No. PCT/GB03/00857 filed Mar. 3, 2003, the entire disclosure of which is incorporated herein by reference.

BACKGROUND OF THE INVENTION

Organic light emitting diodes (OLEDS) are an emerging display technology. In essence an OLED (or organic electroluminescent device) comprises a thin organic layer or stack of organic layers sandwiched between two electrodes, such that when a voltage is applied, light is emitted. At least one of the electrodes must be transparent to visible light.

There are two principal techniques that can be used to deposit the organic layers in an OLED: thermal evaporation and solution processing. Solution processing has the potential to be the lower cost technique due to its potentially greater throughput and ability to handle large substrate sizes. However, several manufacturing issues still have to be resolved before solution processing of OLEDs can fulfil its potential. In a multi-colour or full-colour display the emissive organic layers need to be patterned according to the pixel layout. High-resolution displays require a high-resolution pattern for the emissive layer. To date, solution-processing techniques for patterning the emissive layer are far from ideal.

Recent advances in OLED efficiencies have been made using phosphorescent rather than fluorescent emitters. Simple spin statistics would predict that one singlet exciton is formed for every three triplet excitons. In most organic compounds only the singlet states are emissive, so the maximum potential internal efficiency is 25%. (Note, however, that the simple spin statistics may not be applicable to conjugated polymers.) However, in phosphorescent compounds, the triplet states are emissive, which allows a greater proportion of the excitons to be utilised. Phosphorescent compounds typically have strong spin-orbit coupling, for example due to the presence of a heavy element, such as Ir or Pt. In many cases, the most efficient OLED devices have multi-layer structures (e.g. WO 00/57676 and U.S. Pat. No. 6,303,238). Such multi-layer structures can be formed by thermal evaporation, but when solution-processing techniques are used, depositing a second layer may wash away the first layer.

In an organic light-emitting display the organic light-emitting layer is generally divided into individual pixels, which can be switched between emitting and non-emitting states by altering the current flow through them. In general, the pixels are arranged in orthogonal rows and columns, and two arrangements for addressing the pixels are in common use: passive matrix and active matrix. In a passive-matrix device, one of the electrodes is patterned in rows and the other in columns, and each pixel can be made to emit light by applying an appropriate voltage between the row and column electrodes that intersect at the pixel in question. Each row is addressed in turn for a fraction of the frame time. There is a practical limit on the number of rows that can be driven with a passive-matrix addressing scheme. In an active-matrix display, circuitry (typically a transistor or combination of transistors) is provided for each pixel so that each pixel can be left in an emitting state while another pixel is addressed. Integration of the active-matrix circuitry and the organic light-emitting device is more complicated than for a passive matrix display but active-matrix OLEDs are expected to have benefits in terms of size of display, power consumption and lifetime.

It has been recognised that if a photolithographic technique could be successfully applied to the patterning of the organic layers in an OLED then this would offer many benefits. Photolithographic techniques are established in other industries and can give good resolution and high throughput. However the attempts to use photolithography during the formation of the organic layers in OLEDs have all had only very limited success.

BASF (U.S. Pat. No. 5,518,824) discusses the principle of forming an OLED using a crosslinkable charge-transporting material. The material is deposited from solution, and then exposed to UV light, which crosslinks the material making it insoluble. Subsequent luminescent or electron transporting layers can be deposited on top of the insoluble layer. BASF mentions that if the UV exposure is carried out through a mask, then the exposed areas will be insoluble and the unexposed areas still soluble, and developing (washing) this film in solvent will remove the unexposed material, leaving the insoluble patterned material. However, this patterning is not demonstrated. BASF discuss doping the film with a fluorescent dye or using a crosslinkable fluorescent dye (U.S. Pat. No. 5,922,481) to form the light-emitting layer. The EL device results reported by BASF from its crosslinked devices are very poor. The two devices reported, which have crosslinked but un-patterned light emitting layers, give light emission only at 87 V and 91 V, respectively, both of which are entirely unacceptable operating voltages for an OLED.

Bayerl et al. (Macromolecules 1999, 20, 224-228) used crosslinked oxetane-bisfunctionalized N,N,N',N'-tetraphenyl-benzidine as the hole-transporting material in a two-layer device, in which the electron-transporting layer consisted of a poly(α-methylstyrene) matrix doped with 2-biphenyl-5-(4-tert-butylphenyl)-3,4-oxadiazol (50 wt %) and the emitter perylene (1 wt %). This device gave blue emission. However, they did not pattern the hole-transporting material. Bacher et al. (Macromolecules 1999, 32, 4551-4557) demonstrated photo-crosslinking of a hole-transporting material. They produced a patterned photo-crosslinked hole-transport layer on to which they deposited an emissive layer (tris(8-hydroxyquinoline)aluminium: Alq$_3$), and made a functioning OLED device. However, they had not developed a technique for photo-lithographically patterning the emissive layer, and unless the emissive layer can also be patterned, only a monochrome device can be formed.

The present invention is directed to OLEDs that solve some of the problems in the prior art.

SUMMARY OF THE INVENTION

According to one aspect, the present invention provides a composition comprising a mixture of (A) a polymerisable compound, which undergoes polymerisation on exposure to heat or to actinic radiation, having the general formula

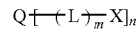

wherein Q is an organic charge transporting fragment, L is a linker group, X is a group capable of undergoing free radical or anionic polymerisation on exposure to heat or actinic radiation, m is 0 or 1, and n is an integer having a value of 2 or more; and (B) a phosphorescent material.

According to a second aspect, the present invention provides a solid film comprising a heat-induced or a radiation-induced polymerisation reaction product of a composition comprising a mixture of (A) a polymerisable compound, which undergoes polymerisation on exposure to heat or to actinic radiation, having the general formula

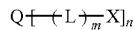

wherein Q is an organic charge transporting fragment, L is a linker group, X is a group capable of undergoing free radical or anionic polymerisation on exposure to heat or actinic radiation, m is 0 or 1, and n is an integer having a value of 2 or more: and (B) a phosphorescent material.

According to a third aspect, the present invention provides a laminate comprising at least two solid films according to the second aspect.

According to a further aspect, the present invention provides an organic light emitting device comprising, laminated in sequence, a substrate, electrode, light emitting layer and counter electrode wherein the light emitting layer is a film according to the above second aspect or a laminate according to the above third aspect.

According to a yet further aspect, the present invention provides a method of making a light emitting layer for use in an organic light emitting device which method comprises forming a film of a composition comprising a mixture of (A) a polymerisable compound, which undergoes polymerisation on exposure to heat or to actinic radiation, having the general formula

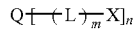

wherein Q is an organic charge transporting fragment, L is a linker group, X is a group capable of undergoing free radical or anionic polymerisation on exposure to heat or actinic radiation, m is 0 or 1, and n is an integer having a value of 2 or more: and (B) a phosphorescent material and exposing the film to heat or actinic radiation to induce polymerisation of the polymerisable compound.

According to a yet still further aspect, the present invention provides a method of forming a multicolour organic light emitting layer comprising the steps of (i) forming a film of a composition of the invention which is capable of emitting light of a first colour;

(ii) exposing the film to actinic radiation through a mask;

(iii) removing unexposed material from the film to leave a predetermined pattern of exposed material;

(iv) forming, on the predetermined pattern of exposed material obtained in step (iii), a film of a composition of the invention which is capable of emitting light of a second colour different from the first colour; and (v) exposing the film formed in step (iv) to actinic radiation through a mask. The method may, if desired, comprise the further steps:

(vi) removing unexposed material from the film exposed in step (v) to leave a predetermined pattern of exposed material;

(vii) forming, on the predetermined pattern of exposed material obtained in step (vi), a film of a composition of the invention which is capable of emitting light of a third colour which is different from the first and second colours; and (viii) exposing the film formed in step (vii) to actinic radiation through a mask.

DETAILED DESCRIPTION OF THE INVENTION

The composition of the present invention comprises a mixture of (A) a polymerisable compound, which undergoes polymerisation on exposure to heat or to actinic radiation, having the general formula

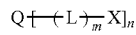

wherein Q is an organic charge transporting fragment, L is a linker group, X is a group capable of undergoing free radical or anionic polymerisation on exposure to heat or actinic radiation, m is 0 or 1, and n is an integer having a value of 2 or more: and (B) a phosphorescent material.

The charge-transporting fragment is preferably a bipolar or hole-transporting fragment, although an electron-transporting fragment could also be used. The triplet energy level of Q is positioned such that there can be effective energy transfer to the phosphorescent material, i.e. the triplet energy level of Q must be comparable with or slightly above the energy level of the emissive state of the phosphorescent material. As an organic species, Q will preferably have a long-lived triplet excited state.

The phosphorescent material is preferably the minor component in the film.

X is a group capable of undergoing thermal- or photo-initiated free radical or anionic polymerisation. For free radical polymerisation, X is preferably an acrylic group, for example acrylate, methacrylate, acrylonitrile, methacrylonitrile, acrylamide, and methacrylamide. Also useful are vinyl compounds, especially vinyl aromatic compounds, for example styrene, alkylstyrene, halostyrene, vinylnaphthalene, or N-vinylcarbazole. X can also be a vinyl group which is in conjugation with the rest of the molecule, Q. Moreover, vinyl esters of monocarboxylic and polycarboxylic acids, N-vinyllactams such as N-vinylpyrrolidone, vinyl ethers of monohydroxy and polyhydroxy compounds, allyl compounds, for example allyl esters of monocarboxylic and polycarboxylic acids and allyl ethers of monocarboxylic and polycarboxylic compounds can also be used. For anionic polymerisation X is preferably a cyclic ether such as an epoxide. X is preferably connected to Q by a linker group, L. Examples of preferred linker groups include —(CH$_2$)$_p$—, where p is 1 to 6, or —(CH$_2$)$_r$—O—(CH$_2$)$_s$—, where r+s is 1 to 6. Alternative linker groups include thioether, ester or amide.

An OLED device according to the invention comprises, laminated in sequence, a substrate, electrode, light emitting layer and counter electrode wherein the light emitting layer is a film comprising a heat- or radiation-induced polymerisation product of the composition described above or a laminate of two or more such films. The film is preferably made by a process comprising i) depositing a film of a composition of the invention ii) exposing said film to actinic radiation (for example, UV light, visible light, electron beams or X-rays), optionally through a mask iii) optionally washing the exposed film to remove any unexposed material.

Preferably, the actinic radiation is visible or UV light.

The OLED can be part of a passive-matrix display or an active-matrix display, however, we believe that phosphorescent materials can be used advantageously with active-matrix addressed OLEDs in particular to give improved device efficiencies.

As is well known in the field there may be additional functional layers in the OLED. There may be a hole-transporting layer between the anode and the light emitting layer, and a hole-blocking layer and/or electron-transporting layer(s) between the light-emitting layer and the cathode. A hole-blocking layer between the phosphorescent light-emitting layer and the cathode is particularly beneficial. The light-emitting layer may also contain photo-initiator or other components. Following washing or developing of the film, the film may be dried or undergo other post-patterning treatment.

The light-emitting layer is preferably patterned, that is a suitable photo-mask is used when the film is exposed to light. This patterning technique allows a multi-colour OLED to be formed. A film that emits a first colour is deposited, patterned and developed to form pixels of the first colour. At this stage, since the film of the first colour is crosslinked it is insoluble, which allows a film of the second colour material to be deposited without disrupting the first colour. This second film is patterned and developed to form pixels of the second colour. The process can be repeated to deposit a third colour.

A solution-processing technique, such as spin-coating, ink-jet printing, dip-coating meniscus or roller coating, or other printing or coating technique such as thermal transfer, is used to deposit the light-emitting layer.

Suitable phosphorescent materials for use in the composition of the invention include heavy transition metal complexes. The phosphorescent material is preferably an organometallic complex of iridium for example Ir(ppy)$_3$ (fac tris(2-phenylpyridine)iridium), which gives green emission (see Baldo et al., *Appl. Phys. Lett.*, 75 no.1, 1999, 4), or (btp$_2$)Ir (acac) (bis(2-(2'-benzo[4,5-α]thienyl)pyridinato-N,C$^{3'}$)iridium(acetyl-acetonate)), which gives red emission (see Adachi et al., *Appl. Phys. Lett.*, 78 no.11, 2001, 1622). It could, instead, be a complex of platinum, for example 2,3,7,8,12,13,17,18-octaethyl-21H,23H-porphine platinum (PtOEP) which gives red emission. The phosphorescent material could also be a molecular or dendritic species, for example an iridium-cored dendrimer.

The concentration of the phosphorescent material in the host material should be such that the film has a high photoluminescent and electroluminescent efficiency. If the concentration of the emissive species is too high, quenching of luminescence can occur. A concentration in the range 0.5-15 molar %, more preferably 2-6 molar %, is generally appropriate.

In the polymerisable host, Q—[-(L-)mX]n, the charge-transporting fragment, Q, preferably contains at least one carbazole or arylamine unit. More preferably, Q contains at least two carbazole units. Q can be based on known hole-transporting arylamine materials such as those with the formula

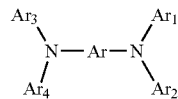

where Ar is an optionally substituted aromatic group, such as phenyl, or

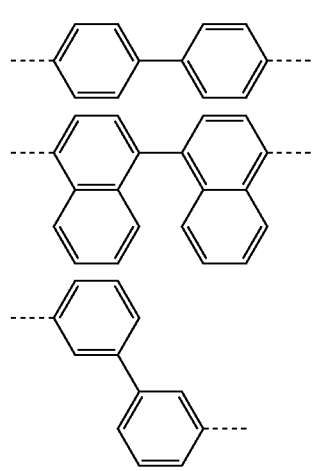

and Ar$_1$, Ar$_2$, Ar$_3$ and Ar$_4$ are optionally substituted aromatic or heteroaromatic groups. Ar is preferably biphenyl. At least two of Ar$_1$, Ar$_2$, Ar$_3$ and Ar$_4$ are bonded to a cross-linkable group, X. Ar$_1$ and Ar$_2$, and/or Ar$_3$ and Ar$_4$ are optionally linked to form a N containing ring, for example so that the N forms part of a carbazole unit eg.

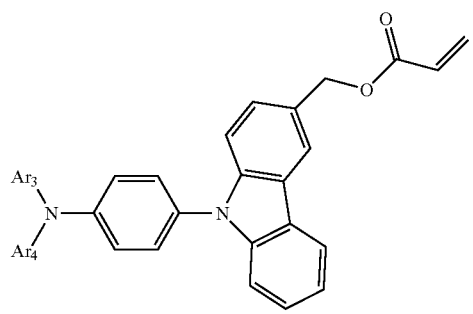

In a preferred embodiment the polymerisable charge-transport material is a derivative of CBP (4,4'-bis(carbazol-9-yl)biphenyl), or TCTA (4,4',4"-tris(carbazol-9-yl)triphenylamine); see Ikai et al. (*Appl. Phys. Lett.*, 79 no. 2, 2001, 156) for a discussion of previously used hosts for phosphorescent dopants. The polymerisable group, X, is preferably acrylate or methacrylate. Hence a preferred example of the polymerisable host is:

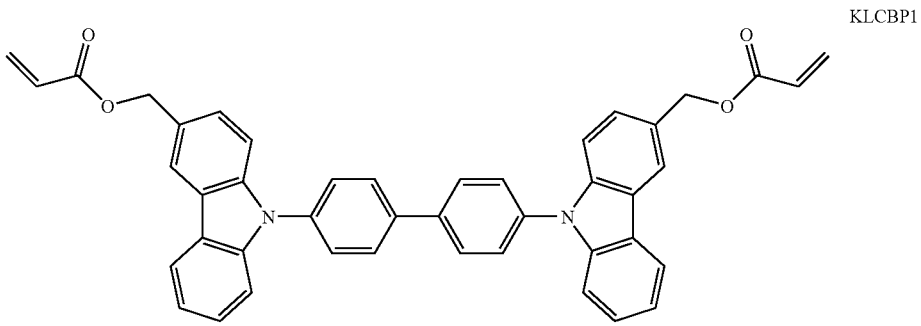

KLCBP1

As can be seen from the example, there is a linker group —CH$_2$— between the charge-transporting moiety and the acrylate group. Such a linker group improves the film forming properties of the material, allowing good quality films to be deposited from solution. The linker group also aids the polymerisation process.

In an alternative embodiment X is styrene and the polymerisable host is

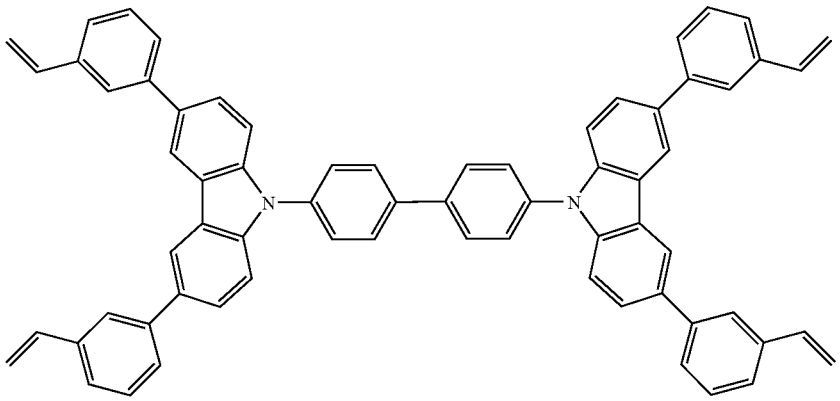

The host material must have at least two polymerisable groups to form a crosslinked network. A crosslinked network is necessary to ensure the film is insoluble after polymerisation. The film could contain a mixture of monomers, with different monomers having different numbers of polymerisable functional groups.

In another embodiment, Q is an electron-transporting material such as an aryl substituted oxadiazole or an aryl substituted triazole of which specific examples include TAZ (3-phenyl-4-(1-naphthyl)-5-phenyl-1,2,4-triazole) and OXD-7 (1,3-bis(N,N-t-butyl-phenyl)-1,3,4-oxadiazole).

Acrylate derivatives can be easily photo-polymerised, and good resolution can be obtained in patterned films. For acrylate systems there are suitable known initiators for activation by either UV light or visible light. For successful initiation, it is generally preferable to use a wavelength of light that is absorbed by the initiator but not strongly absorbed by the other components of the film. In this way the initiator functions well and photo-degradation of the film is minimised. One advantage of the current invention, in which the major component of the film is the charge transporting layer, is that the band gap of charge-transporting materials is generally larger than that of luminescent species, and hence it is easier to find a wavelength of light which is not more strongly absorbed than it is in systems in which the major component of the film contains the chromophore.

It had not previously been known whether phosphorescent materials would be sufficiently stable to the photo-polymerisation of the acrylate moieties, nor what the device performance would be. Reported results from photo-polymerised crosslinked acrylate systems with fluorescent dopants are very poor. The inventors have found that the films described in this invention are sufficiently stable to the polymerisation process and give much better OLED device results than the previously reported systems. Changing from a fluorescent emitter to a phosphorescent emitter could potentially increase the efficiency by a factor of four (spin statistics). However, we have unexpectedly found a much greater increase in efficiency than could be accounted for solely by this change.

The inventors have examined cured films of Ir(ppy)$_3$ doped in KLCBP1 and found that the film can be washed with solvent without washing Ir(ppy)$_3$ from the film, even though the Ir(ppy)$_3$ is not chemically bound in the film and is in a relatively high concentration. In contrast, when some fluorescent dyes were doped into similar films they did wash out of the films. It would be possible, if desired, to modify the phosphorescent compound so that it contained a polymerisable functional group. Then such a phosphorescent compound could be co-polymerised with the host material.

A further advantage of the current system is that the inventors have found that films of Ir(ppy)$_3$ in KLCBP1 can be crosslinked by exposure to light, even when no separate initiator has been added to the film. It is advantageous for OLED performance to avoid using an initiator. An initiator is likely, at least partly, to remain in the film, even after development, and may have a deleterious effect on the OLED efficiency or lifetime.

Devices made from such materials have higher efficiency than any previous reports of OLEDs with photo-patterned emissive layers.

EXAMPLES

Synthesis of 4,4'-bis(3-(acryloyloxymethyl)carbazol-9-yl) (KLCBP1)

Synthesis of the 4,4'-bis(3-formylcarbazol-9-yl)biphenyl (2)

Figure 1:
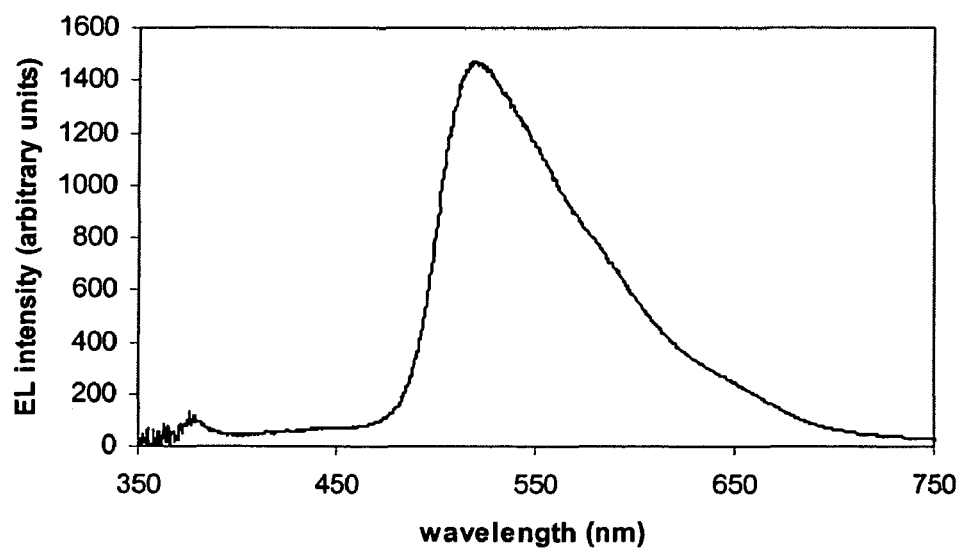
FIG. 1 shows the electroluminescent (EL) emission spectrum of a device containing Ir(ppy)$_3$ in a crosslinked acrylate host.

Phosphorus oxychloride (13.0 ml, 21.5 g, 140 mmol) was added dropwise to a stirring mixture of N,N-dimethylformamide (5.40 ml, 5.10 g, 69.7 mmol) and 4,4'-bis(carbazol-9-yl)biphenyl (1) (7.72 g, 16.0 mmol) and the resulting mixture was stirred at room temperature for 5 minutes then heated to 90° C. for 24 h. The reaction mixture was poured into water (800 ml) and the flask containing the product was placed in the ultrasonic bath for 2 hours to break up the material. The mixture was stirred for 2 hours then filtered. The residue was washed with water (500 ml) followed by hexane (500 ml) and dried at the pump for 2 hours. The crude product, a brown solid, was heated at reflux with acetone (3×400 ml) and filtered. The product, 4,4'-bis(3-formylcarbazol-9-yl)-biphenyl, (2) (7.92 g, 87%) was obtained as an cream solid with

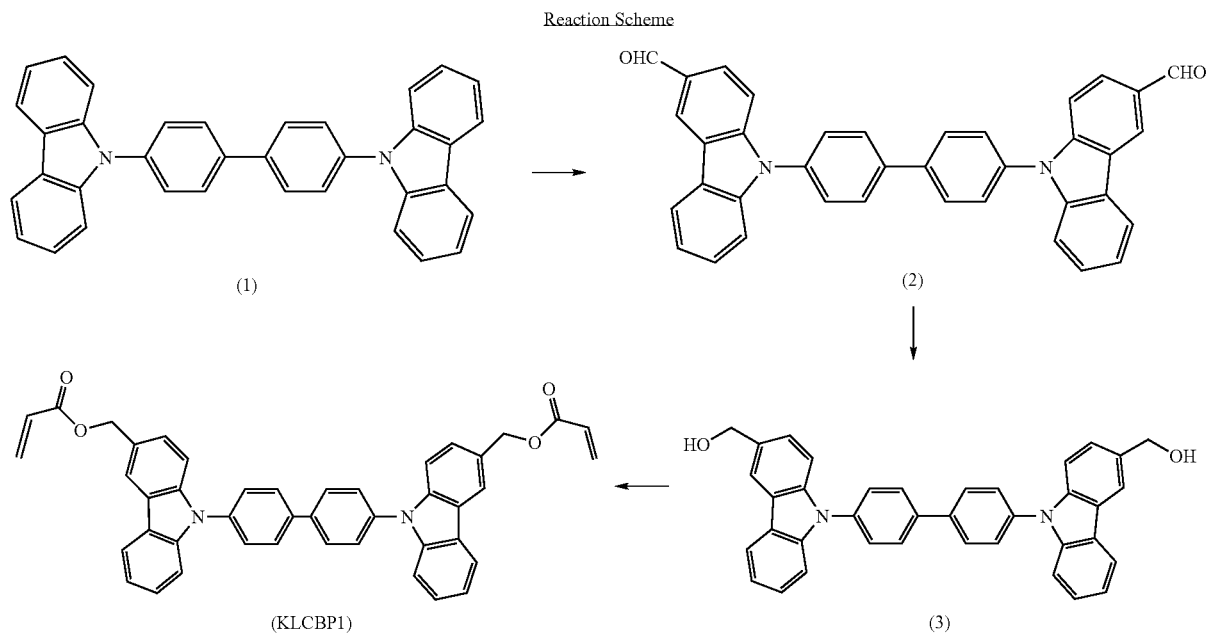

Reaction Scheme

Synthesis of 4,4'-bis(carbazol-9-yl)biphenyl (CBP) (1)

Tri-tert-butylphosphine (304 mg, 1.50 mmol) in toluene (38 ml) was added under nitrogen to a deoxygenated mixture of carbazole (16.9 g, 0.100 mmol), 4,4'-dibromobiphenyl (15.7 g, 50.4 mmol), sodium tert-butoxide (30.9 g, 321 mmol) and palladium acetate (115 mg, 0.512 mmol) in toluene (50 ml) and the resulting mixture was heated at reflux under nitrogen for 10 days. The reaction mixture was cooled to room temperature and then diluted with more toluene (200 ml). The reaction mixture was filtered to remove the sodium salts. The filtrate was concentrated to dryness to give the crude product as a pale brown solid. The crude product was purified first by chromatography on silica using dichloromethane as the eluent followed by recrystallisation from toluene. The material was then sublimed at 280-281° C. at $10^{-6}$ mm Hg to give the product 4,4'-bis(carbazol-9-yl)biphenyl (1) (18.3 g, 75%), as an off-white solid with melting point 280-281° C. (lit. m.p. 281° C.).

melting point 295° C. (dec). $^1$H n.m.r.: (300 MHz, Me$_2$SO): δ 10.09 (2H, s, CHO); 8.88 (2H, d, J 0.88 Hz, aromatic H); 8.41 (2H, d, J 7.61 Hz, aromatic H); 8.41 (4H, d, J 8.49 Hz, aromatic H); 8.00 (2H, dd, J 8.49, 1.46 Hz, aromatic H); 7.83 (4H, d, J 8.49 Hz, aromatic H); 7.61-7.38 (8H, m, aromatic H). $\lambda_{max}$(CH$_2$Cl$_2$): 215 nm (ε/Lmor$^{-1}$cm$^{-1}$ 9163), 241 (68 488), 272 (65 928), 294 (67 194) 328 (42 620). FT-IR (solid): 3045, 2825, 2730, 1682, 1623, 1591, 1505, 1456, 1438, 1365, 1319, 1275, 1230, 1180, 802, 745 cm$^{-1}$. m/z (TOF) 540 (M$^+$).

Synthesis of the 4,4'-bis(3-(hydroxymethyl)carbazol-9-yl)biphenyl (3)

Sodium borohydride (2.40 g, 63.4 mmol)) was added to the 4,4'-bis(3-formyl-carbazol-9-yl)biphenyl (2) (3.42 g, 6.33 mmol) in THF (1.2 L) and the resulting suspension was stirred at room temperature for 24 h. Once the reaction was complete, the mixture was slowly poured into water (400 ml) and the mixture was left to stir at room temperature for a further 30 min. The reaction mixture was acidified to pH 6 with hydrochloric acid (5M) and the product was extracted with dichloromethane (3×300 ml). The combined organic phase was washed with water (400 ml) and brine (400 ml), dried (MgSO$_4$), filtered and the filtrate evaporated to dryness. The crude product was purified by chromatography on silica using 50% THF/toluene as the eluent The product, 4,4'-bis(3-(hydroxymethyl)carbazol-9-yl)(3) was obtained as a pale yellow solid (3.22 g, 94%) with m.p. 268° C. (dec). $^1$H n.m.r.: (300 MHz, CDCl$_3$): δ 8.23 (2H, d, J 7.61 Hz, aromatic H); 8.18 (2H, s, aromatic H); 8.06 (4H, d, J 8.19 Hz, aromatic H); 7.75 (4H, J 8.19 Hz, aromatic H); 7.50-7.38 (8H, m, aromatic H), 7.29 (2H, m, aromatic H); 5.25 (2H, t, J 5.58 Hz, OH); 4.68 (4H, d, J 5.56 Hz, CH$_2$). $\lambda_{max}$(CH$_2$Cl$_2$): 216 nm (ε/Lmol$^{-1}$cm$^{-1}$ 177 455), 240 (57 873), 271 (56 595), 294 (55 330) 329 (37 758). FTIR (solid): 3343, 1604, 1500, 1485, 1455, 1362, 1330, 1230, 803, 745 cm$^{-1}$. m/z (TOF) 544 (M$^+$).

Synthesis of 4,4'-bis(3-(acryloyloxymethyl)carbazol-9-yl) (KLCBP1)

Acryloyl chloride (0.613 g, 0.550 ml, 6.77 mmol) in dichloromethane (20 ml) was added dropwise to a mixture of the diol (3) (1.41 g, 2.58 mmol) and triethylamine (1.09 g, 1.50 ml, 10.8 mmol) in dichloromethane (500 ml) and the resulting mixture was stirred at room temperature for 2 h. The solvent, excess triethylamine and acryloyl chloride were removed under reduced pressure without heating (to avoid polymerisation) and the crude product was dried for a further 30 min to ensure that all reagents had been evaporated. The crude product was dissolved in dichloromethane (150 ml) and the organic phase was washed with water (2×200 ml) and brine (200 ml), dried (MgSO$_4$), filtered and the filtrate evaporated to dryness. The product was recrystallised from ethanol to give the product, 4,4'-bis(3-(acryloyloxymethyl)carbazol-9-yl), as a cream solid (1.48 g, 88%) with melting point 68° C. $^1$H n.m.r.: (300 MHz, CDCl$_3$): δ 8.19 (2H, s, aromatic H); 8.16 (2H, d, J 7.91 Hz, aromatic H); 7.90 (4H, d, J 8.48 Hz, aromatic H); 7.68 (4H, d, J 8.48, aromatic H); 7.51-7.41 (8 H, m, aromatic H); 7.31 (2H, m, aromatic H); 6.46 (2H, dd, J$_{trans}$ 17.57, J$_{gem}$ 1.46 Hz, C═C—H); 6.18 (2H, dd, J$_{trans}$ 17.26, J$_{cis}$ 10.53 Hz, C═C—H); 5.84 (2H, dd, J$_{cis}$ 10.24, J$_{gem}$ 1.46 Hz, C═C—H); 5.40 (4H, s, CH$_2$). FT-IR (solid): 3039, 2972, 1718, 1631, 1604, 1501, 1456, 1404, 1362, 1294, 1231, 1179, 1044, 806, 746 cm$^{-1}$. $\lambda_{max}$(CH$_2$Cl$_2$): 240 nm (ε/Lmol$^{-1}$cm$^{-1}$ 82 245), 294 (37 245), 316 (27 565). PL: $\lambda_{max}$ (solid) 374 nm with CIE coordinates x=0.174, y=0.032, PL: $\lambda_{max}$ (CHCl$_2$) 381 nm with CIE coordinates x=0.165, y=0.021. m/z (TOF) 652 (M$^+$).

Fabrication of Phosphorescent Emitter Doped Photo-Crosslinked OLEDs

Ir(ppy)$_3$ (4 wt %) and the monomer KLCBP1 were dissolved in pure chloroform at total concentration 10 mg ml−1. The solutions were spun onto ITO coated glass substrates (previously cleaned by ultrasonication in commercial detergent and thorough rinsing with Dl water). Prior to spin-coating the dry ITO coated glass was plasma-treated in an Emitech K1050X plasma unit (process gas oxygen, 100 W, 2 min). Solutions were spun onto the ITO substrates at 2000 rpm with acceleration 500 rs$^{-1}$ for a total of 60 s giving an emitting organic layer of thickness ca 50 nm. Films were then photopolymerized under an inert atmosphere (N$_2$) using a Hanovir UVA 250 W U.V source. The films were irradiated for 3 minutes through a 5"×5" glass photo mask (cut-off 360 nm) giving a rectangular exposed area 15×20 mm. The photopolymerized films were developed by rinsing with pure toluene, dried under a stream of dry nitrogen and transferred to the evaporator (KJLesker) for completion of the OLED by evaporation of the electron-transporting layer/hole-blocking layer (ETL/HBL) and top electrode. TPBI deposited by vacuum evaporation formed the ETUHBL (60 nm). LiF (0.5 nm) and Aluminium (100-150 nm) deposited by vacuum evaporation formed the cathode.

Device performance: 3.4 cd/A (@105 cd/m$^2$), 0.44 lm/W (@24.2 V), ToV (turn-on voltage) 17.0 V. These results not only show a significantly reduced turn-on voltage compared with previously reported OLEDs with crosslinked acrylate emissive layers. They also show improved luminous power efficiency (0.44 IM/W) compared with previously reported OLEDs with photo-patterned emissive layers. The electroluminescent spectrum is shown in FIG. 1. The peak in the emission spectrum occurs at 520 nm.

The device results above compare favourably with those from a similar device with the inclusion of an initiator, i.e. Ir(ppy)$_3$ (4 wt %) doped into a KLCBP1 monomer host with 0.5 wt % HNu470 initiator (Spectra Group Limited). For this device the following summarizes the results: 1.1 cd/A (@101 cd/m$^2$), 0.15 lm/W (@21.6 V), ToV (turn-on voltage) 15.6V.

Example 2

Synthesis of Bis[3,6(3-vinylphenyl)-carbazol-9-vl]bipheny) (CBP-st$_4$)

Scheme 1 describes the synthesis of CBP-st$_4$

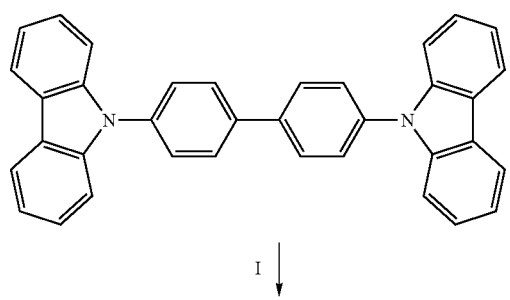

I ↓

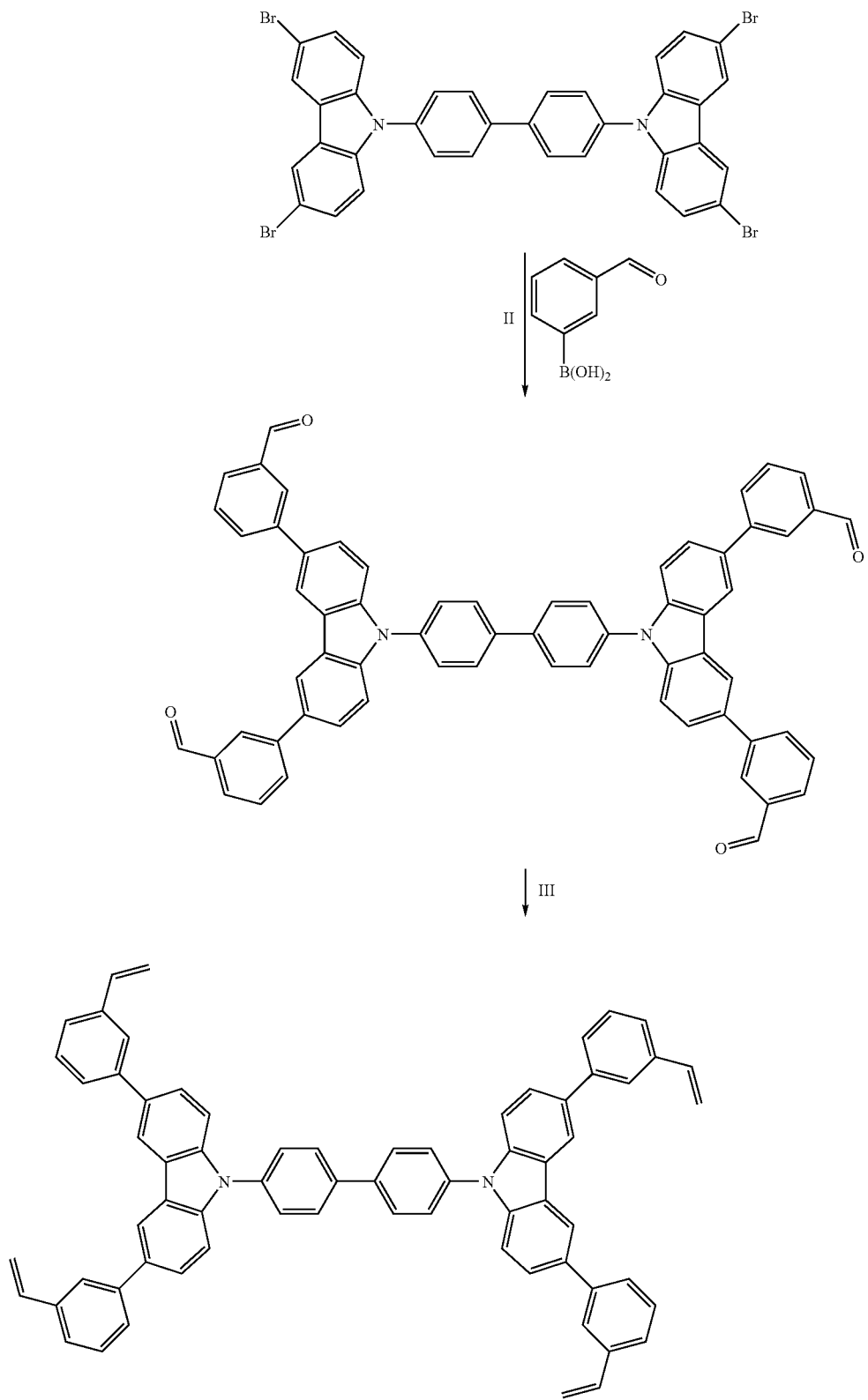
Scheme 1: i. Br₂ in DCM ii. Pd(PPh₃)₄, Na₂CO₃, EtOH, Toluene iii MePh₃PBr, KOBuᵗ in THF Synthesis of 4,4'-bis(carbazol-9-yl)biphenyl (CBP)

see example 1

4,4'-bis(3,6-dibromocarbazol-9-yl)biphenyl (CBP-Br$_4$)

Bromine (2.0 ml, 6.22 g, 38.9 mmol) in dichloromethane (50 ml) was added dropwise to a solution of CBP (3.56 g, 7.35 mmol) in dichloromethane (500 ml). The reaction mixture was stirred at room temperature for a further 20 h, then heated at reflux for a further 10 h. The reaction mixture was cooled to room temperature and the precipitate was filtered off and dried at the pump. The product was washed with dichloromethane (200 ml) and hexane (200 ml) and the material was dried under vacuum for a further 3 hours. The product, 4,4'-bis(2,3-dibromocarbazol-9-yl)biphenyl, was obtained as a white precipitate with m.p. 380° C. (dec.). The product was found to be insoluble in all organic solvents. Found: C, 54.29; H, 2.58; and N, 3.69. $C_{36}H_{20}N_2Br_4$. requires C, 54.04; H, 2.52; N, 3.50%).

Synthesis of Bis[3,6(3-formylphenyl)-carbazol-9-yl]biphenyl

Bis(3,6-dibromocarbazol-9-yl)biphenyl (2.90 g, 1.67 mmol) and 3-formyl-phenylboronic acid (2.21 g, 14.7 mmol) were combined then toluene (50 ml), ethanol (20 ml) and a solution of sodium carbonate (2M, 20 ml) were added with stirring then mixture was deoxygenated by bubbling a stream of nitrogen through the solution. Tetrakis(triphenylphosphine)palladium (170 mg, 0.147 mmol) was added and the mixture was heated at reflux for 5 days (oil bath temperature was set to 100° C.). The reaction mixture was cooled to room temperature then poured into water (100 ml). Dichloromethane (150 ml) was added and the organic phase was separated. The aqueous phase was extracted twice more with dichloromethane (2×50 ml). The organic phases were combined then washed with water (200 ml) and brine (150 ml), dried over magnesium sulfate and filtered. The filtrate was evaporated to dryness to give the crude product as a pale brown solid. The product was purified by chromatography on silica using a mixture (1:99) of ethanol and dichloromethane as the eluent. The relevant fractions were combined and the product, bis[3,6(3-formylphenyl)-carbazol-9-yl]biphenyl was obtained as a yellow solid (2.01 g, 62%) with m.p. 285-290° C. (dec). $^1$H n.m.r (300 MHz, CDCl$_3$): δ 7.60-7.69, m, 8 ArH; 7.70-7.80, m, 8 ArH; 7.88, d, 4 ArH, J 7.62 Hz; 7.96-8.06, m, 8 ArH; 8.28, s, 4 ArH; 10.15, s, 4 CHO. UV: (CHCl$_3$) λ 256 nm (ε68 709), 296 (49 448). FT-IR: (solid) 1698, 1602, 1505, 1473, 1362, 1286, 1231, 1180, 1159783, 754 cm$^{-1}$. UV: (CHCl$_3$) λ 256 nm (s 68 709), 296 (49 448).

Synthesis of Bis[3,6(3-vinylphenyl)-carbazol-9-yl]biphenyl) (CBP-st$_4$)

Methyltriphenylphosphonium bromide (3.10 g, 8.68 mmol) and potassium tert-butoxide (0.973 g, 8.67 mmol) were combined under nitrogen and the mixture was deoxygenated further under vacuum then backfilled with nitrogen. Freshly distilled THF (100 ml) was added under nitrogen and the resulting mixture, a bright yellow suspension, was stirred at room temperature for 20 min. The tetraaldehyde was added and the resulting mixture was stirred for a further 3 h. The reaction mixture was diluted with dichloromethane and filtered through cellite. The filtrate was evaporated to dryness and a bright yellow crude product was obtained. The product was purified by chromatography on silica using an 80% mixture of dichloromethane/hexane as the eluent. The relevant fractions were combined, the solvent removed under reduced pressure and the product was evaporated to dryness. The product, bis[3,6(3-formylphenyl)-carbazol-9-yl]biphenyl, was obtained as a white solid (0.765 g, 60%) with m.p. 268° C. (dec.). Found: C, 91.18; H, 5.25; N, 3.15. Calculated for $C_{68}H_{48}N_2$: C, 91.45; H, 5.42; N, 3.14. $^1$H n.m.r (300 MHz, CDCl$_3$): δ 5.26, d, 4 vinyl H, $J_{cis}$ 10.5 Hz; 5.81, d, 4 vinyl H, $J_{trans}$ 17.6 Hz; 6.78, dd, 4 vinyl H, $J_{trans}$ 17.6, $J_{cis}$ 10.5 Hz; 7.30-7.45, m, 8 ArH; 7.50-7.72, m, 20 ArH; 7.87, d, 4 ArH, J 8.25 Hz; 8.37, s, 4 ArH. UV: (CHCl$_3$) λ 257 nm (ε159 273), 297 (101 667). FT-IR: (solid) 3050, 1596, 1500, 1472, 1450, 1360, 1282, 1227, 1166, 984, 893, 870, 785, 706 cm$^{-1}$.

Fabrication of an OLED Containing a Photo-Crosslinked Emissive Layer Comprising a Styryl-Derivative and a Phosphorescent Dopant Ir(ppy)$_3$ (7 wt %) was used as the emitter doped in the tetra-styryl substituted CBP monomer CBP-st$_4$. The formulation was dissolved in pure chloroform at total concentration 7 mg ml$^{-1}$. The solutions were spun onto ITO coated glass substrates (previously cleaned by ultrasonication in commercial detergent and thorough rinsing with DI water). Prior to spin-coating the dry ITO coated glass was plasma-treated in an Emitech K1050X plasma unit (process gas oxygen, 100 W, 2 min). Solutions were spun onto the ITO substrates at 2000 rpm with acceleration 500 rs$^{-1}$ for a total of 30 s giving an emitting organic layer of thickness ca 50 nm. Films were then photopolymerized under an inert atmosphere (N$_2$) using a Hanovir UVA 250 W UV source. The films were irradiated for 4 minutes through a 5"×5" glass photo mask (cut-off 360 nm) giving a rectangular exposed area 15×20 mm. Overlap of this area with ITO anode and deposited aluminium cathode defines active areas consisting of 6 pixels measuring 4×5 mm. The photopolymerized films were developed by double-immersion in pure toluene, dried under a stream of dry nitrogen and transferred to the evaporator (KJLesker) for completion of the OLED by evaporation of ETUHBL and top electrode. TPBI deposited by vacuum evaporation formed the ETL/HBL (50 nm). LiF (1.2 nm) and Aluminium (100-150 nm) deposited by vacuum evaporation formed the cathode.

Figure 2:
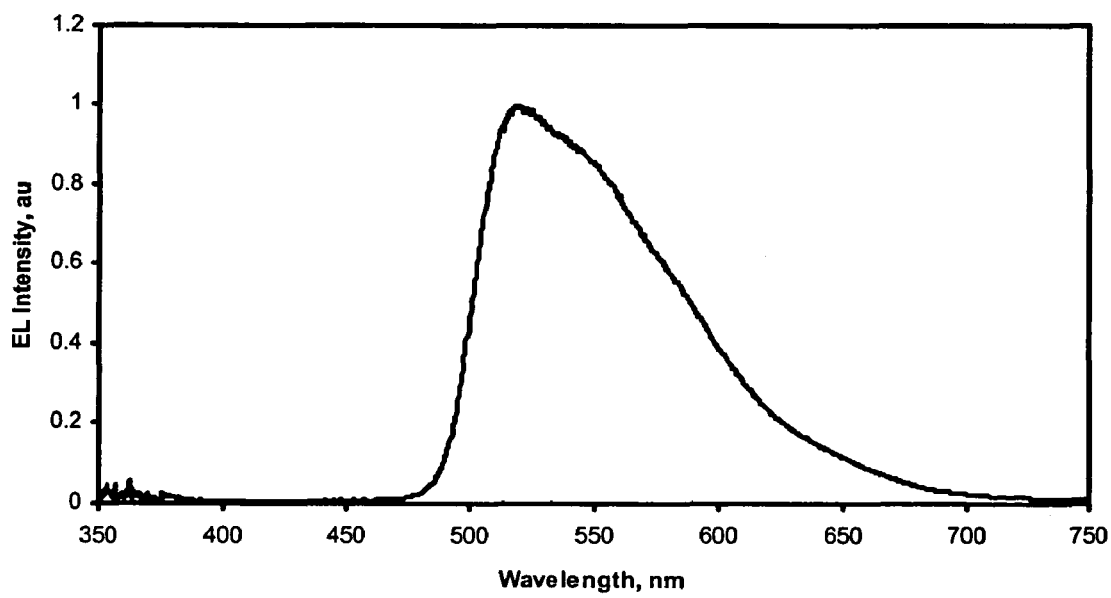
FIG. 2 shows the EL emission spectrum of a device containing Ir(ppy)$_3$ in a crosslinked styrene host.

Device Performance for CBP6-st$_4$:Ir(ppy)
6.0 cd/A (@120.4 cd/m2), 2.10 lm/W (@9.0 V), ToV 6.2 V
Max EQE 6.04 cd/A (@62 cd/m2, 2.26 lm/W, 8.4 V)
Max PE 2.70 lm/W (@<10 cd/m2, 5.90 cd/A, 7.0 V)
CIE coords x=0.36 y=0.59
The EL emission spectrum is shown in FIG. 2.
device structure ITO/CBP-st$_4$:Ir(ppy)/TPBI/LiF/Al This device containing a styryl-derivative (CPB-st$_4$) has a lower turn-on voltage than the device containing the acrylate-derivative (KLCBP1). The efficiency is also higher. It should be noted that the formulation comprised only the monomer and the phosphorescent dopant and that no separate initiator was added. This combination of materials cured well without requiring a specific initiator. As in the previous example the phosphorescent dopant is not chemically bound in the polymerised film.

The invention claimed is:
1. A composition comprising a mixture of
(A) a polymerisable compound, which undergoes polymerisation on exposure to heat or to actinic radiation, having the general formula

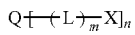

wherein Q is an organic charge transporting fragment, L is a linker group, X is a group capable of undergoing free radical or anionic polymerisation on exposure to heat or actinic radiation, m is 0 or 1, and n is an integer having a value of 2 or more; and (B) a phosphorescent material, wherein the phosphorescent material is present in the mixture at a concentration in the range of from 0.5 molar % to 15 molar %, wherein the phosphorescent material is free of polymerisable functional groups.

2. A composition according to claim 1, wherein the organic charge transporting fragment Q has a triplet energy level which is substantially equal to or slightly greater than the energy level of the emissive state of the phosphorescent material.

3. A composition according to claim 1, wherein X is selected from the group consisting of groups containing ethylenic unsaturation and groups containing a cyclic ether moiety.

4. A composition according to claim 3, wherein X is a group containing an acrylic group, a vinyl group, an allyl group, or an epoxide group.

5. A composition according to claim 1, wherein Q comprises at least one group selected from carbazole and arylamine.

6. A composition according to claim 5, wherein Q has the general formula

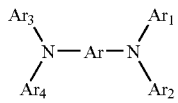

where Ar is an optionally substituted aromatic group and $Ar_1$, $Ar_2$, $Ar_3$ and $Ar_4$ are the same or different optionally substituted aromatic or heteroaromatic groups or $Ar_1$ and $Ar_2$ are linked together to form with the N atom to which they are both attached, a N-containing heterocyclic group and/or $Ar_3$ and $Ar_4$ are linked together to form, with the N atom to which they are both attached, a N-containing heterocyclic group and wherein at least two of $Ar_1$, $Ar_2$, $Ar_3$ and $Ar_4$ are linked to a group $-(L)_m-X$.

7. A composition according to claim 6, wherein $Ar_1$ and $Ar_2$ are linked together to form, with the N atom to which they are both attached, an optionally-substituted carbazole group.

8. A composition according to claim 6, wherein $Ar_3$ and $Ar_4$ are linked together to form, with the N atom to which they are both attached, an optionally-substituted carbazole group.

9. A composition according to claim 1, wherein Q is an electron-transporting group selected from an aryl-substituted oxadiazole group and an aryl-substituted triazole group.

10. A composition according to claim 1, wherein the phosphorescent material is a phosphorescent organometallic complex of a transition metal or a phosphorescent organometallic transition metal dendrimer.

11. A composition according to claim 10, wherein the phosphorescent material is selected from the group consisting of organometallic complexes of iridium, organometallic complexes of platinum, and organometallic iridium dendrimers.

12. A composition according to claim 1 which, additionally, contains at least one initiator.

13. A composition according to claim 1, wherein the composition does not contain a separate initiator.

14. A method of making a light emitting layer comprising the steps of forming a film of a composition of claim 1 and exposing the film to heat or actinic radiation to induce polymerisation of the polymerisable compound.

15. A method of making a light emitting layer according to claim 14 comprising exposing the film to actinic radiation to induce polymerisation of the polymerisable compound.

16. A method according to claim 15 comprising exposing the film to actinic radiation through a mask and then developing the exposed film to remove unexposed material.

17. A method of forming a multicolour organic light emitting layer comprising the steps of
(i) forming a film of a composition of claim 1 capable of emitting light of a first colour;
(ii) exposing the film to actinic radiation through a mask;
(iii) removing unexposed material from the film to leave a predetermined pattern of exposed material;
(iv) forming, on the predetermined pattern of exposed material obtained in step (iii), a film of a composition of claim 1 which is capable of emitting light of a second colour different from the first colour; and
(v) exposing the film formed in step (iv) to actinic radiation through a mask.

18. A method of forming a multicolour organic light emitting layer comprising the steps of
(i) forming a film of a composition of claim 1 capable of emitting light of a first colour;
(ii) exposing the film to actinic radiation through a mask;
(iii) removing unexposed material from the film to leave a predetermined pattern of exposed material;
(iv) forming, on the predetermined pattern of exposed material obtained in step (iii), a film of a composition of claim 1 which is capable of emitting light of a second colour different from the first colour;
(v) exposing the film formed in step (iv) to actinic radiation through a mask,
(vi) removing unexposed material from the film exposed in step (v) to leave a predetermined pattern of exposed material;
(vii) forming, on the predetermined pattern of exposed material obtained in step (vi), a film of a composition of claim 1 which is capable of emitting light of a third colour different from the first and second colours; and
(viii) exposing the film formed in step (vii) to actinic radiation through a mask.

19. The composition according to claim 1, wherein the phosphorescent material is present in the mixture at a concentration in the range of from 2 molar % to 6 molar %.

* * * * *

UNITED STATES PATENT AND TRADEMARK OFFICE
CERTIFICATE OF CORRECTION

PATENT NO. : 7,736,534 B2
APPLICATION NO. : 10/506914
DATED : June 15, 2010
INVENTOR(S) : Neil Maxted et al.

It is certified that error appears in the above-identified patent and that said Letters Patent is hereby corrected as shown below:

In the Specification:

At Column 1, line 23, "fulfil" should be -- fulfill --;

At Column 10, line 19, "an" should be -- a --;

At Column 12, line 47, "Bis[3,6(3-vinylphenyl)-carbazol-9-vl]bipheny)" should be -- Bis[3,6(3-vinylphenyl)-carbazol-9-yl]biphenyl) --.

Signed and Sealed this
Twenty-second Day of February, 2011

David J. Kappos
*Director of the United States Patent and Trademark Office*